(12) United States Patent
Heiliger (10) Patent No.: US 11,123,132 B2
(45) Date of Patent: Sep. 21, 2021

(54) MULTI-FUNCTION SURGICAL INSTRUMENTS AND ASSEMBLIES THEREFOR

(71) Applicant: COVIDIEN LP, Mansfield, MA (US)

(72) Inventor: Zachary S. Heiliger, Nederland, CO (US)

(73) Assignee: Covidien LP, Mansfield, MA (US)

( * ) Notice: Subject to any disclaimer, the term of this patent is extended or adjusted under 35 U.S.C. 154(b) by 836 days.

(21) Appl. No.: 15/948,544

(22) Filed: Apr. 9, 2018

(65) Prior Publication Data

US 2019/0307502 A1  Oct. 10, 2019

(51) Int. Cl.
| | |
|---|---|
| *A61B 18/14* | (2006.01) |
| *A61B 17/32* | (2006.01) |
| *A61B 18/00* | (2006.01) |
| *A61B 18/12* | (2006.01) |
| *A61B 34/35* | (2016.01) |

(Continued)

(52) U.S. Cl.
CPC .. *A61B 18/1445* (2013.01); *A61B 17/320016* (2013.01); *A61B 34/35* (2016.02); *A61B 34/37* (2016.02); *A61B 2017/2901* (2013.01); *A61B 2017/2902* (2013.01); *A61B 2017/2912* (2013.01); *A61B 2017/2932* (2013.01); *A61B 2018/00172* (2013.01); *A61B 2018/00601* (2013.01); *A61B 2018/00982* (2013.01);
(Continued)

(58) Field of Classification Search
CPC ...... A61B 18/00172; A61B 2017/2901; A61B 18/1445; A61B 17/320016; A61B 2017/2902; A61B 34/35; A61B 34/37
See application file for complete search history.

(56) References Cited

U.S. PATENT DOCUMENTS

| | | |
|---|---|---|
| 4,005,714 A | 2/1977 | Hiltebrandt |
| D249,549 S | 9/1978 | Pike |
| | (Continued) | |

FOREIGN PATENT DOCUMENTS

| | | |
|---|---|---|
| AU | 2011253698 A1 | 12/2011 |
| CN | 201299462 Y | 9/2009 |
| | (Continued) | |

*Primary Examiner* — Jaymi E Della
*Assistant Examiner* — Sean W Collins
(74) *Attorney, Agent, or Firm* — Carter, DeLuca & Farrell LLP (57) ABSTRACT

An inner guide assembly and surgical instrument including the same wherein the inner guide assembly includes a proximal tube guide defining first and second proximal channels extending longitudinally therealong, a distal tube guide defining first and second distal channels extending longitudinally therealong and disposed in alignment with the first and second proximal channels, respectively, and a wire clip disposed between the proximal and distal tube guides and defining a central channel having a first portion and a second portion. The first proximal channel, the first distal channel, and the first portion of the central channel are configured to cooperate to receive a first elongated component of a surgical instrument longitudinally therethrough. The second proximal channel, the second distal channel, and the second portion of the central channel are configured to cooperate to receive first and second lead wires of the surgical instrument longitudinally therethrough.

20 Claims, 9 Drawing Sheets

(51) Int. Cl.
*A61B 34/37* (2016.01)
*A61B 17/29* (2006.01)

(52) U.S. Cl.
CPC . *A61B 2018/126* (2013.01); *A61B 2018/1253* (2013.01); *A61B 2018/1455* (2013.01)

(56) References Cited

U.S. PATENT DOCUMENTS

| | | | |
|---|---|---|---|
| D263,020 S | 2/1982 | Rau, III | |
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| 5,026,379 A | 6/1991 | Yoon | |
| D343,453 S | 1/1994 | Noda | |
| 5,312,391 A | 5/1994 | Wilk | |
| 5,318,589 A | 6/1994 | Lichtman | |
| 5,324,254 A | 6/1994 | Phillips | |
| D348,930 S | 7/1994 | Olson | |
| D349,341 S | 8/1994 | Lichtman et al. | |
| 5,342,359 A | 8/1994 | Rydell | |
| 5,368,600 A | 11/1994 | Failla et al. | |
| D354,564 S | 1/1995 | Medema | |
| 5,401,274 A | 3/1995 | Kusunoki | |
| D358,887 S | 5/1995 | Feinberg | |
| 5,411,519 A | 5/1995 | Tovey et al. | |
| 5,445,638 A | 8/1995 | Rydell et al. | |
| 5,458,598 A | 10/1995 | Feinberg et al. | |
| 5,527,313 A | 6/1996 | Scott et al. | |
| 5,556,397 A | 9/1996 | Long et al. | |
| 5,611,813 A | 3/1997 | Lichtman | |
| D384,413 S | 9/1997 | Zlock et al. | |
| 5,735,873 A | 4/1998 | MacLean | |
| H001745 H | 8/1998 | Paraschac | |
| 5,792,164 A | 8/1998 | Lakatos et al. | |
| 5,807,393 A | 9/1998 | Williamson, IV et al. | |
| D402,028 S | 12/1998 | Grimm et al. | |
| D408,018 S | 4/1999 | McNaughton | |
| 5,893,863 A | 4/1999 | Yoon | |
| 5,919,202 A | 7/1999 | Yoon | |
| D416,089 S | 11/1999 | Barton et al. | |
| 6,004,319 A | 12/1999 | Goble et al. | |
| D424,694 S | 5/2000 | Tetzlaff et al. | |
| D425,201 S | 5/2000 | Tetzlaff et al. | |
| 6,113,596 A | 9/2000 | Hooven et al. | |
| H001904 H | 10/2000 | Yates et al. | |
| 6,156,009 A | 12/2000 | Grabek | |
| 6,190,386 B1 | 2/2001 | Rydell | |
| 6,270,497 B1 | 8/2001 | Sekino et al. | |
| D449,886 S | 10/2001 | Tetzlaff et al. | |
| 6,299,625 B1 | 10/2001 | Bacher | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| 6,387,094 B1 | 5/2002 | Eitenmuller | |
| H002037 H | 7/2002 | Yates et al. | |
| D465,281 S | 11/2002 | Lang | |
| D466,209 S | 11/2002 | Bon | |
| 6,551,313 B1 | 4/2003 | Levin | |
| 6,558,385 B1 | 5/2003 | McClurken et al. | |
| 6,679,882 B1 | 1/2004 | Kornerup | |
| D493,888 S | 8/2004 | Reschke | |
| D496,997 S | 10/2004 | Dycus et al. | |
| 6,808,525 B2 | 10/2004 | Latterell et al. | |
| D499,181 S | 11/2004 | Dycus et al. | |
| 6,837,888 B2 | 1/2005 | Ciarrocca et al. | |
| D502,994 S | 3/2005 | Blake, III | |
| D509,297 S | 9/2005 | Wells | |
| 6,942,662 B2 | 9/2005 | Goble et al. | |
| 7,033,356 B2 | 4/2006 | Latterell et al. | |
| 7,063,699 B2 | 6/2006 | Hess et al. | |
| D525,361 S | 7/2006 | Hushka | |
| D531,311 S | 10/2006 | Guerra et al. | |
| 7,128,254 B2 | 10/2006 | Shelton, IV et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| 7,208,005 B2 | 4/2007 | Frecker et al. | |
| D541,611 S | 5/2007 | Aglassinger | |
| D541,938 S | 5/2007 | Kerr et al. | |
| D545,432 S | 6/2007 | Watanabe | |
| 7,232,440 B2 | 6/2007 | Dumbauld et al. | |
| D547,154 S | 7/2007 | Lee | |
| D564,662 S | 3/2008 | Moses et al. | |
| D567,943 S | 4/2008 | Moses et al. | |
| 7,367,976 B2 | 5/2008 | Lawes et al. | |
| 7,402,162 B2 | 7/2008 | Ouchi | |
| D575,395 S | 8/2008 | Hushka | |
| D575,401 S | 8/2008 | Hixson et al. | |
| 7,442,194 B2 | 10/2008 | Dumbauld et al. | |
| 7,445,621 B2 | 11/2008 | Dumbauld et al. | |
| D582,038 S | 12/2008 | Swoyer et al. | |
| 7,481,810 B2 | 1/2009 | Dumbauld et al. | |
| 7,510,562 B2 | 3/2009 | Lindsay | |
| 7,588,570 B2 | 9/2009 | Wakikaido et al. | |
| 7,658,311 B2 | 2/2010 | Boudreaux | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| 7,758,577 B2 | 7/2010 | Nobis et al. | |
| D621,503 S | 8/2010 | Otten et al. | |
| 7,789,878 B2 | 9/2010 | Dumbauld et al. | |
| 7,815,636 B2 | 10/2010 | Ortiz | |
| 7,819,872 B2 | 10/2010 | Johnson et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 7,879,035 B2 | 2/2011 | Garrison et al. | |
| D649,249 S | 11/2011 | Guerra | |
| D649,643 S | 11/2011 | Allen, IV et al. | |
| D661,394 S | 6/2012 | Romero et al. | |
| 8,257,352 B2 | 9/2012 | Lawes et al. | |
| 8,333,765 B2 | 12/2012 | Johnson et al. | |
| 8,353,437 B2 | 1/2013 | Boudreaux | |
| 8,454,602 B2 | 6/2013 | Kerr et al. | |
| 8,523,898 B2 | 9/2013 | Bucciaglia et al. | |
| 8,529,566 B2 | 9/2013 | Kappus et al. | |
| 8,568,408 B2 | 10/2013 | Townsend et al. | |
| 8,591,510 B2 | 11/2013 | Allen, IV et al. | |
| 8,628,557 B2 | 1/2014 | Collings et al. | |
| 8,679,098 B2 | 3/2014 | Hart | |
| 8,679,140 B2 | 3/2014 | Butcher | |
| RE44,834 E | 4/2014 | Dumbauld et al. | |
| 8,685,009 B2 | 4/2014 | Chernov et al. | |
| 8,685,056 B2 | 4/2014 | Evans et al. | |
| 8,696,667 B2 | 4/2014 | Guerra et al. | |
| 8,702,737 B2 | 4/2014 | Chojin et al. | |
| 8,702,749 B2 | 4/2014 | Twomey | |
| 8,745,840 B2 | 6/2014 | Hempstead et al. | |
| 8,747,413 B2 | 6/2014 | Dycus | |
| 8,747,434 B2 | 6/2014 | Larson et al. | |
| 8,752,264 B2 | 6/2014 | Ackley et al. | |
| 8,756,785 B2 | 6/2014 | Allen, IV et al. | |
| 8,845,636 B2 | 9/2014 | Allen, IV et al. | |
| 8,852,185 B2 | 10/2014 | Twomey | |
| 8,864,753 B2 | 10/2014 | Nau, Jr. et al. | |
| 8,864,795 B2 | 10/2014 | Kerr et al. | |
| 8,887,373 B2 | 11/2014 | Brandt et al. | |
| 8,888,771 B2 | 11/2014 | Twomey | |
| 8,900,232 B2 | 12/2014 | Ourada | |
| 8,920,461 B2 | 12/2014 | Unger et al. | |
| 8,939,972 B2 | 1/2015 | Twomey | |
| 8,961,513 B2 | 2/2015 | Allen, IV et al. | |
| 8,961,514 B2 | 2/2015 | Garrison | |
| 8,961,515 B2 | 2/2015 | Twomey et al. | |
| 8,968,283 B2 | 3/2015 | Kharin | |
| 8,968,298 B2 | 3/2015 | Twomey | |
| 8,968,305 B2 | 3/2015 | Dumbauld et al. | |

(56) References Cited

U.S. PATENT DOCUMENTS

| | | |
|---|---|---|
| 8,968,306 B2 | 3/2015 | Unger |
| 8,968,307 B2 | 3/2015 | Evans et al. |
| 8,968,308 B2 | 3/2015 | Horner et al. |
| 8,968,309 B2 | 3/2015 | Roy et al. |
| 8,968,310 B2 | 3/2015 | Twomey et al. |
| 8,968,311 B2 | 3/2015 | Allen, IV et al. |
| 8,968,317 B2 | 3/2015 | Evans et al. |
| 8,968,360 B2 | 3/2015 | Garrison et al. |
| 9,011,435 B2 | 4/2015 | Brandt et al. |
| 9,023,035 B2 | 5/2015 | Allen, IV et al. |
| 9,028,492 B2 | 5/2015 | Kerr et al. |
| 9,033,981 B2 | 5/2015 | Olson et al. |
| 9,034,009 B2 | 5/2015 | Twomey et al. |
| 9,039,691 B2 | 5/2015 | Moua et al. |
| 9,039,704 B2 | 5/2015 | Joseph |
| 9,039,732 B2 | 5/2015 | Sims et al. |
| 9,060,780 B2 | 6/2015 | Twomey et al. |
| 9,113,882 B2 | 8/2015 | Twomey et al. |
| 9,113,899 B2 | 8/2015 | Garrison et al. |
| 9,113,901 B2 | 8/2015 | Allen, IV et al. |
| 9,113,909 B2 | 8/2015 | Twomey et al. |
| 9,113,933 B2 | 8/2015 | Chernova et al. |
| 9,113,934 B2 | 8/2015 | Chernov et al. |
| 9,113,938 B2 | 8/2015 | Kerr |
| 9,161,807 B2 | 10/2015 | Garrison |
| 2002/0049442 A1 | 4/2002 | Roberts et al. |
| 2004/0236326 A1 | 11/2004 | Schulze et al. |
| 2005/0187547 A1 | 8/2005 | Sugi |
| 2006/0129146 A1 | 6/2006 | Dycus et al. |
| 2007/0078458 A1 | 4/2007 | Dumbauld et al. |
| 2007/0106295 A1 | 5/2007 | Garrison et al. |
| 2007/0213707 A1 | 9/2007 | Dumbauld et al. |
| 2007/0278277 A1 | 12/2007 | Wixey et al. |
| 2008/0083813 A1 | 4/2008 | Zemlok et al. |
| 2008/0215050 A1 | 9/2008 | Bakos |
| 2008/0243120 A1 | 10/2008 | Lawes et al. |
| 2009/0012556 A1 | 1/2009 | Boudreaux et al. |
| 2009/0112206 A1 | 4/2009 | Dumbauld et al. |
| 2009/0125026 A1 | 5/2009 | Rioux et al. |
| 2009/0125027 A1 | 5/2009 | Fischer |
| 2009/0131974 A1 | 5/2009 | Pedersen et al. |
| 2009/0171350 A1 | 7/2009 | Dycus et al. |
| 2009/0182327 A1 | 7/2009 | Unger |
| 2009/0254084 A1 | 10/2009 | Naito |
| 2010/0185196 A1 | 7/2010 | Sakao et al. |
| 2010/0185197 A1 | 7/2010 | Sakao et al. |
| 2010/0292690 A1 | 11/2010 | Livneh |
| 2011/0009863 A1 | 1/2011 | Marczyk et al. |
| 2011/0071525 A1 | 3/2011 | Dumbauld et al. |
| 2011/0087218 A1 | 4/2011 | Boudreaux et al. |
| 2011/0130757 A1 | 6/2011 | Horlle et al. |
| 2011/0264093 A1 | 10/2011 | Schall |
| 2011/0276049 A1 | 11/2011 | Gerhardt |
| 2011/0319886 A1 | 12/2011 | Chojin et al. |
| 2012/0083827 A1 | 4/2012 | Artale et al. |
| 2012/0209263 A1 | 8/2012 | Sharp et al. |
| 2012/0239034 A1 | 9/2012 | Horner et al. |
| 2012/0259331 A1 | 10/2012 | Garrison |
| 2012/0265241 A1 | 10/2012 | Hart et al. |
| 2012/0296205 A1 | 11/2012 | Chernov et al. |
| 2012/0296238 A1 | 11/2012 | Chernov et al. |
| 2012/0296239 A1 | 11/2012 | Chernov et al. |
| 2012/0296323 A1 | 11/2012 | Chernov et al. |
| 2012/0296371 A1 | 11/2012 | Kappus et al. |
| 2012/0303026 A1 | 11/2012 | Dycus et al. |
| 2012/0323238 A1 | 12/2012 | Tyrrell et al. |
| 2012/0330308 A1 | 12/2012 | Joseph |
| 2012/0330351 A1 | 12/2012 | Friedman et al. |
| 2013/0018364 A1 | 1/2013 | Chernov et al. |
| 2013/0022495 A1 | 1/2013 | Allen, IV et al. |
| 2013/0071282 A1 | 3/2013 | Fry |
| 2013/0072927 A1 | 3/2013 | Allen, IV et al. |
| 2013/0079760 A1 | 3/2013 | Twomey et al. |
| 2013/0079774 A1 | 3/2013 | Whitney et al. |
| 2013/0085496 A1 | 4/2013 | Unger et al. |
| 2013/0103030 A1 | 4/2013 | Garrison |
| 2013/0103031 A1 | 4/2013 | Garrison |
| 2013/0138101 A1 | 5/2013 | Kerr |
| 2013/0144284 A1 | 6/2013 | Behnke, II et al. |
| 2013/0144306 A1* | 6/2013 | Stefanchik ............ A61B 34/70 606/130 |
| 2013/0165907 A1 | 6/2013 | Attar et al. |
| 2013/0197503 A1 | 8/2013 | Orszulak |
| 2013/0218198 A1 | 8/2013 | Larson et al. |
| 2013/0245623 A1 | 9/2013 | Twomey |
| 2013/0247343 A1 | 9/2013 | Horner et al. |
| 2013/0253489 A1 | 9/2013 | Nau, Jr. et al. |
| 2013/0255063 A1 | 10/2013 | Hart et al. |
| 2013/0267948 A1 | 10/2013 | Kerr et al. |
| 2013/0267949 A1 | 10/2013 | Kerr |
| 2013/0274736 A1 | 10/2013 | Garrison |
| 2013/0282010 A1 | 10/2013 | McKenna et al. |
| 2013/0289561 A1 | 10/2013 | Waaler et al. |
| 2013/0296854 A1 | 11/2013 | Mueller |
| 2013/0296922 A1 | 11/2013 | Allen, IV et al. |
| 2013/0296923 A1 | 11/2013 | Twomey et al. |
| 2013/0304058 A1 | 11/2013 | Kendrick |
| 2013/0304059 A1 | 11/2013 | Allen, IV et al. |
| 2013/0304066 A1 | 11/2013 | Kerr et al. |
| 2013/0310832 A1 | 11/2013 | Kerr et al. |
| 2013/0325057 A1 | 12/2013 | Larson et al. |
| 2013/0331837 A1 | 12/2013 | Larson |
| 2013/0338666 A1 | 12/2013 | Bucciaglia et al. |
| 2013/0338693 A1 | 12/2013 | Kerr et al. |
| 2013/0345701 A1 | 12/2013 | Allen, IV et al. |
| 2013/0345706 A1 | 12/2013 | Garrison |
| 2013/0345735 A1 | 12/2013 | Mueller |
| 2014/0005663 A1 | 1/2014 | Heard et al. |
| 2014/0005666 A1 | 1/2014 | Moua et al. |
| 2014/0025052 A1 | 1/2014 | Nau, Jr. et al. |
| 2014/0025053 A1 | 1/2014 | Nau, Jr. et al. |
| 2014/0025059 A1 | 1/2014 | Kerr |
| 2014/0025060 A1 | 1/2014 | Kerr |
| 2014/0025066 A1 | 1/2014 | Kerr |
| 2014/0025067 A1 | 1/2014 | Kerr et al. |
| 2014/0025070 A1 | 1/2014 | Kerr et al. |
| 2014/0025073 A1 | 1/2014 | Twomey et al. |
| 2014/0031821 A1 | 1/2014 | Garrison |
| 2014/0031860 A1 | 1/2014 | Stoddard et al. |
| 2014/0046323 A1 | 2/2014 | Payne et al. |
| 2014/0066910 A1 | 3/2014 | Nau, Jr. |
| 2014/0066911 A1 | 3/2014 | Nau, Jr. |
| 2014/0074091 A1 | 3/2014 | Arya et al. |
| 2014/0100564 A1 | 4/2014 | Garrison |
| 2014/0100568 A1 | 4/2014 | Garrison |
| 2014/0276797 A1 | 9/2014 | Batchelor et al. |
| 2014/0309677 A1* | 10/2014 | Baldwin ........ A61B 17/320016 606/170 |
| 2015/0073462 A1* | 3/2015 | Guba ................. A61B 17/295 606/170 |

FOREIGN PATENT DOCUMENTS

| | | |
|---|---|---|
| DE | 2415263 A1 | 10/1975 |
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 4242143 A1 | 6/1994 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 B4 | 3/1999 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009318 U1 | 8/2007 |

(56) References Cited

FOREIGN PATENT DOCUMENTS

| | | |
|---|---|---|
| DE | 202007009317 U1 | 10/2007 |
| DE | 10031773 B4 | 11/2007 |
| DE | 202007016233 U1 | 1/2008 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| EP | 1530952 | 5/2005 |
| EP | 2316367 A1 | 5/2011 |
| EP | 2853221 A1 | 4/2015 |
| EP | 2982326 A1 | 2/2016 |
| JP | 61501068 | 9/1984 |
| JP | 1147150 A | 6/1989 |
| JP | 6502328 | 3/1992 |
| JP | 55106 | 1/1993 |
| JP | 0540112 | 2/1993 |
| JP | 0006030945 A | 2/1994 |
| JP | 6121797 A | 5/1994 |
| JP | 6285078 A | 10/1994 |
| JP | 06343644 A | 12/1994 |
| JP | 6511401 | 12/1994 |
| JP | 07265328 A | 10/1995 |
| JP | H0856955 | 5/1996 |
| JP | 08252263 A | 10/1996 |
| JP | 8289895 A | 11/1996 |
| JP | 8317934 A | 12/1996 |
| JP | 8317936 A | 12/1996 |
| JP | 09000538 A | 1/1997 |
| JP | H0910223 A | 1/1997 |
| JP | 9122138 A | 5/1997 |
| JP | 0010000195 A | 1/1998 |
| JP | H1024051 A | 1/1998 |
| JP | 10155798 A | 6/1998 |
| JP | 1147149 | 2/1999 |
| JP | 11070124 A | 3/1999 |
| JP | 11169381 A | 6/1999 |
| JP | 11192238 A | 7/1999 |
| JP | 11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001008944 A | 1/2001 |
| JP | 2001029355 | 2/2001 |
| JP | 2001029356 A | 2/2001 |
| JP | 2001003400 | 4/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2006015078 A | 1/2006 |
| JP | 2006501939 A | 1/2006 |
| JP | 2006095316 A | 4/2006 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A2 | 6/2002 |
| WO | 2006021269 A1 | 3/2006 |
| WO | 2005110264 A3 | 4/2006 |
| WO | 2007118608 A1 | 10/2007 |
| WO | 2008040483 A1 | 4/2008 |
| WO | 2011018154 A1 | 2/2011 |

\* cited by examiner

MULTI-FUNCTION SURGICAL INSTRUMENTS AND ASSEMBLIES THEREFOR

BACKGROUND

Technical Field

The present disclosure relates to surgical instruments and, more particularly, to multi-function surgical instruments and assemblies therefor.

Background of Related Art

Bipolar surgical instruments typically include two generally opposing electrodes charged to different electric potentials to selectively apply energy to tissue. Bipolar electrosurgical forceps, for example, utilize both mechanical clamping action and electrical energy to treat, e.g., cauterize, coagulate, desiccate, and/or seal, tissue. Once tissue is treated, it is often desirable to cut the treated tissue. Accordingly, many forceps have been designed which incorporate a knife that effectively severs the tissue after tissue treatment.

Monopolar surgical instruments, on the other hand, include an active electrode, and are used in conjunction with a remote return electrode, e.g., a return pad, to apply energy to tissue. Monopolar instruments have the ability to rapidly move through tissue and dissect through narrow tissue planes.

In some surgical procedures, it may be beneficial to use both bipolar and monopolar instrumentation, e.g., procedures where it is necessary to dissect through one or more layers of tissue in order to reach underlying tissue(s) to be treated. Further, it may be beneficial, particularly with respect to endoscopic surgical procedures, to provide a single instrument incorporating both bipolar and monopolar features, thereby obviating the need to alternatingly remove and insert the bipolar and monopolar instruments in favor of one another.

As can be appreciated, as additional functional components are added to a surgical instrument, additional deployment structures or deployment structures capable of actuating more than one component are required. However, multiple deployment structures and/or combined deployment structures may be limited by spatial constraints within the housing or shaft of the surgical instrument, functional constraints of the components, and/or may overly complicate the operable components of the surgical instrument.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

Provided in accordance with aspects of the present disclosure is an inner guide assembly for a surgical instrument including a proximal tube guide, a distal tube guide, and a wire clip. The proximal tube guide defines first and second proximal channels extending longitudinally therealong. The distal tube guide defines first and second distal channels extending longitudinally therealong disposed in alignment with the first and second proximal channels, respectively. The wire clip is disposed between the proximal and distal tube guides and defines a central channel having a first portion and a second portion. The first proximal channel, the first distal channel, and the first portion of the central channel are configured to cooperate to receive a first elongated component of a surgical instrument longitudinally therethrough. The second proximal channel, the second distal channel, and the second portion of the central channel are configured to cooperate to receive first and second lead wires of the surgical instrument longitudinally therethrough.

In an aspect of the present disclosure, at least one of the proximal tube guide or the distal tube guide includes a retention finger configured to retain the first elongated component of the surgical instrument in fixed position relative thereto.

In another aspect of the present disclosure, at least one of the proximal tube guide or the distal tube guide includes a rib configured to retain the first elongated component of the surgical instrument in fixed position relative thereto.

In another aspect of the present disclosure, the proximal and distal tube guides further define third proximal and distal channels, respectively, disposed in alignment with one another. The third proximal and distal channels are configured to receive a second elongated component of the surgical instrument therethrough externally of the wire clip.

In still another aspect of the present disclosure, the proximal and distal tube guides further define fourth proximal and distal channels, respectively, disposed in alignment with one another. The fourth proximal and distal channels are configured to receive a third elongated component of the surgical instrument therethrough externally of the wire clip on an opposite side of the wire clip as the second elongated component.

In yet another aspect of the present disclosure, the first, second, third and fourth proximal and distal channels are arranged circumferentially about the proximal and distal tube guides, respectively.

In still yet another aspect of the present disclosure, the wire clip is oriented such that a mouth of the central channel is oppositely oriented relative to mouths of the second proximal and distal channels and similarly relative to mouths of the first proximal and distal channels.

An elongated shaft assembly for a surgical instrument provided in accordance with aspects of the present disclosure includes a proximal tube portion coupled to a manipulation portion of a surgical instrument, a distal tube portion coupled to an end effector assembly of the surgical instrument, a proximal tube guide, a distal tube guide, and a wire clip. The proximal tube guide is at least partially disposed within the proximal tube portion and defines first and second proximal channels extending longitudinally therealong. The distal tube guide is at least partially disposed within the distal tube portion and defines first and second distal channels extending longitudinally therealong in alignment with the first and second proximal channels. The wire clip is disposed between the proximal and distal tube guides and defines a central channel having a first portion and a second portion. The first proximal channel, the first distal channel, and the first portion of the central channel are configured to cooperate to receive a first elongated component operably coupled between the manipulation portion and the end effector assembly of the surgical instrument. The second proximal channel, the second distal channel, and the second portion of the central channel are configured to cooperate to receive first and second lead wires of the surgical instrument longitudinally therethrough to guide the first and second lead wires to the end effector assembly of the surgical instrument.

In an aspect of the present disclosure, the first proximal channel, the first distal channel, and the first portion of the central channel cooperate to receive a support tube therethrough that slidably receives the first elongated component of the surgical instrument.

In another aspect of the present disclosure, the first elongated component is disposed in fixed position relative to the proximal tube guide, the distal tube guide, and the wire clip.

In still another aspect of the present disclosure, the wire clip is engaged about the first elongated component under a bias. Additionally or alternatively, at least one of the proximal tube guide or the distal tube guide includes a rib configured to retain the support tube in fixed position relative thereto.

In yet another aspect of the present disclosure, the proximal and distal tube guides further define third proximal and distal channels, respectively, disposed in alignment with one another. The third proximal and distal channels are configured to receive a second elongated component of the surgical instrument therethrough externally of the wire clip. The second elongated component is operably coupled to the manipulation portion of the surgical instrument and selectively movable relative to the end effector assembly of the surgical instrument.

In still yet another aspect of the present disclosure, the proximal and distal tube guides further define fourth proximal and distal channels, respectively, disposed in alignment with one another and configured to receive a third elongated component of the surgical instrument therethrough externally of the wire clip on an opposite side of the wire clip as the second elongated component. The third elongated component is operably coupled to the manipulation portion of the surgical instrument and selectively movable relative to the end effector assembly of the surgical instrument.

A surgical instrument provided in accordance with aspects of the present disclosure includes a housing including a first actuator, an end effector assembly distally-spaced from the housing, and an elongated shaft assembly extending between and interconnecting the housing and the end effector assembly. The elongated shaft assembly includes a proximal tube portion coupled to the housing, a distal tube portion coupled to the end effector assembly, a proximal tube guide at least partially disposed within the proximal tube portion and defining first and second proximal channels extending longitudinally therealong, a distal tube guide at least partially disposed within the distal tube portion and defining first and second distal channels extending longitudinally therealong in alignment with the first and second proximal channels, respectively, and a wire clip disposed between the proximal and distal tube guides. The wire clip defines a central channel having a first portion and a second portion. The first proximal channel, the first distal channel, and the first portion of the central channel are configured to cooperate to receive a drive shaft operably coupled between the first actuator and the end effector assembly. The second proximal channel, the second distal channel, and the second portion of the central channel are configured to cooperate to receive first and second lead wires longitudinally therethrough to guide the first and second lead wires to the end effector assembly.

In an aspect of the present disclosure, actuation of the first actuator translates the drive shaft relative to the end effector assembly to manipulate the end effector assembly.

In another aspect of the present disclosure, a support tube is provided wherein the first proximal channel, the first distal channel, and the first portion of the central channel cooperate to receive the support tube therethrough while the drive shaft is slidably disposed within the support tube.

In yet another aspect of the present disclosure, the proximal and distal tube guides further define third proximal and distal channels, respectively, disposed in alignment with one another. The third proximal and distal channels are configured to receive a first deployment shaft therethrough externally of the wire clip. The first deployment shaft is operably coupled between a second actuator associated with the housing and a first deployable component selectively deployable relative to the end effector assembly.

In still yet another aspect of the present disclosure, the proximal and distal tube guides further define fourth proximal and distal channels, respectively, disposed in alignment with one another. The fourth proximal and distal channels are configured to receive a second deployment shaft therethrough externally of the wire clip on an opposite side of the wire clip as the first deployable component. The second deployment shaft is operably coupled between a third actuator associated with the housing and a second deployable component selectively deployable relative to the end effector assembly.

In another aspect of the present disclosure, the elongated shaft assembly further includes a fixed outer tube.

BRIEF DESCRIPTION OF THE DRAWINGS

Various aspects of the present disclosure are described herein with reference to the drawings wherein like reference numerals identify similar or identical elements and.

DETAILED DESCRIPTION

Referring generally to FIGS. 1-5, an endoscopic surgical instrument provided in accordance with the present disclosure is shown generally identified by reference numeral 10. Instrument 10, as described below, is configured to operate in both a bipolar mode, e.g., for grasping, treating, and/or mechanically dissecting tissue, and a monopolar mode, e.g., for treating and/or electrically/electromechanically dissecting tissue. Although the present disclosure is shown and described with respect to instrument 10, the aspects and features of the present disclosure are equally applicable for use with any suitable surgical instrument or portion(s) thereof. Obviously, different connections and considerations apply to each particular instrument and the assemblies and/or components thereof; however, the aspects and features of the present disclosure remain generally consistent regardless of the particular instrument, assemblies, and/or components provided.

Continuing with reference to FIGS. 1-5, instrument 10 generally includes a housing 20, a handle assembly 30, a trigger assembly 60, a rotation assembly 70, an elongated shaft assembly 80, an end effector assembly 100, a drive assembly 140, a knife assembly 160, bipolar and monopolar activation assemblies 170, 180, respectively, a monopolar assembly 200, and a deployment and retraction mechanism 300. Elongated shaft assembly 80 extends distally from housing 20 and supports end effector assembly 100 at a distal end thereof. Drive assembly 140 operably couples handle assembly 30 with end effector assembly 100 to enable selective manipulation of jaw members 110, 120 of end effector assembly 100. Knife assembly 160 is operably coupled with trigger assembly 60 to enable selective translation of knife 164 of knife assembly 160 relative to end effector assembly 100. Monopolar assembly 200 is operably coupled with deployment and retraction mechanism 300 to enable selective deployment and retraction of monopolar assembly 200. Rotating assembly 70 is operably coupled to elongated shaft assembly 80 and enables selective rotation of elongated shaft assembly 80, drive assembly 140, trigger assembly 60, end effector assembly 100, and monopolar assembly 200 relative to housing 20. Bipolar and monopolar activation assemblies 170, 180 enable the appropriate energy to be selectively delivered to end effector assembly 100 and monopolar assembly 200, respectively.

Figures 13, 14, 15:
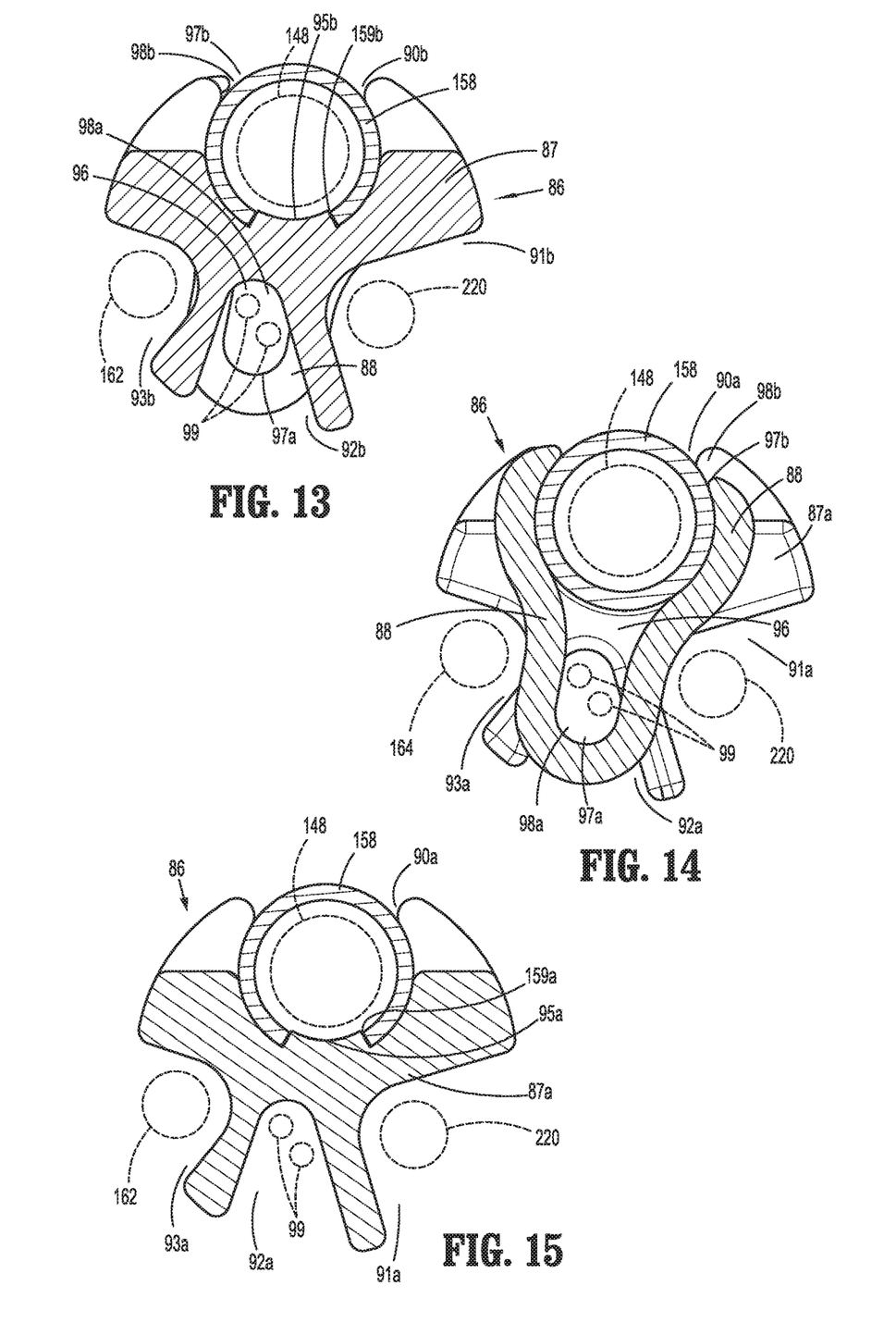
FIG. 13 is an enlarged, transverse, cross-sectional view taken along section line "13-13" of FIG. 6.
FIG. 14 is an enlarged, transverse, cross-sectional view taken along section line "14-14" of FIG. 6.
FIG. 15 is an enlarged, transverse, cross-sectional view taken along section line "15-15" of FIG. 6.

Instrument 10 may also include an electrosurgical cable (not shown) that connects instrument 10 to a generator (not shown) or other suitable power source, although instrument 10 may alternatively be configured as a battery-powered instrument. The electrosurgical cable (not shown) includes wires 99 (FIGS. 13-15) extending therethrough that have sufficient length to extend through housing 20 and/or elongated shaft assembly 80 in order to provide energy to at least one of the electrically-conductive surfaces 112, 122 of jaw members 110, 120, respectively, of end effector assembly 100, e.g., upon activation of bipolar activation switch 172 of bipolar activation assembly 170 in the bipolar mode of operation. Similarly, one or more of the wires of the electrosurgical cable (not shown) extends through housing 20 and/or elongated shaft assembly 80 in order to provide energy to monopolar assembly 200, e.g., upon activation of either of the monopolar activation switches 182 of monopolar activation assembly 180 in the monopolar mode of operation.

Elongated shaft assembly 80 includes a fixed outer tube 82 configured for engagement with housing 20. Fixed outer tube 82 does not extend distally to end effector assembly 100 but, rather, is spaced-apart therefrom, leaving an exposed section of monopolar assembly 200. Elongated shaft assembly 80 further includes an inner proximal tube 83, an inner distal tube 84, and an inner guide assembly 86 including proximal and distal tube guides 87a, 87b, respectively, and a tube clip 88. Inner proximal tube 83 engages rotation assembly 70 and is disposed about a proximal portion of proximal tube guide 87a in engagement therewith. Inner distal tube 84 engages jaw member 120 at the distal end thereof and is disposed about a distal portion of distal tube guide 87b. Inner guide assembly 86 extends between inner proximal tube 83 and inner distal tube 84. Inner proximal tube 83, inner distal tube 84, and inner guide assembly 86 are rotationally coupled with one another such that rotation of inner proximal tube 83 via rotation of rotation assembly 70 effects corresponding rotation of end effector assembly 100, drive assembly 140, knife assembly 160, and monopolar assembly 200 relative to housing 20 (FIG. 1) and fixed outer tube 82. Inner guide assembly 86 of elongated shaft assembly 80 is described in greater detail below.

Figure 1:
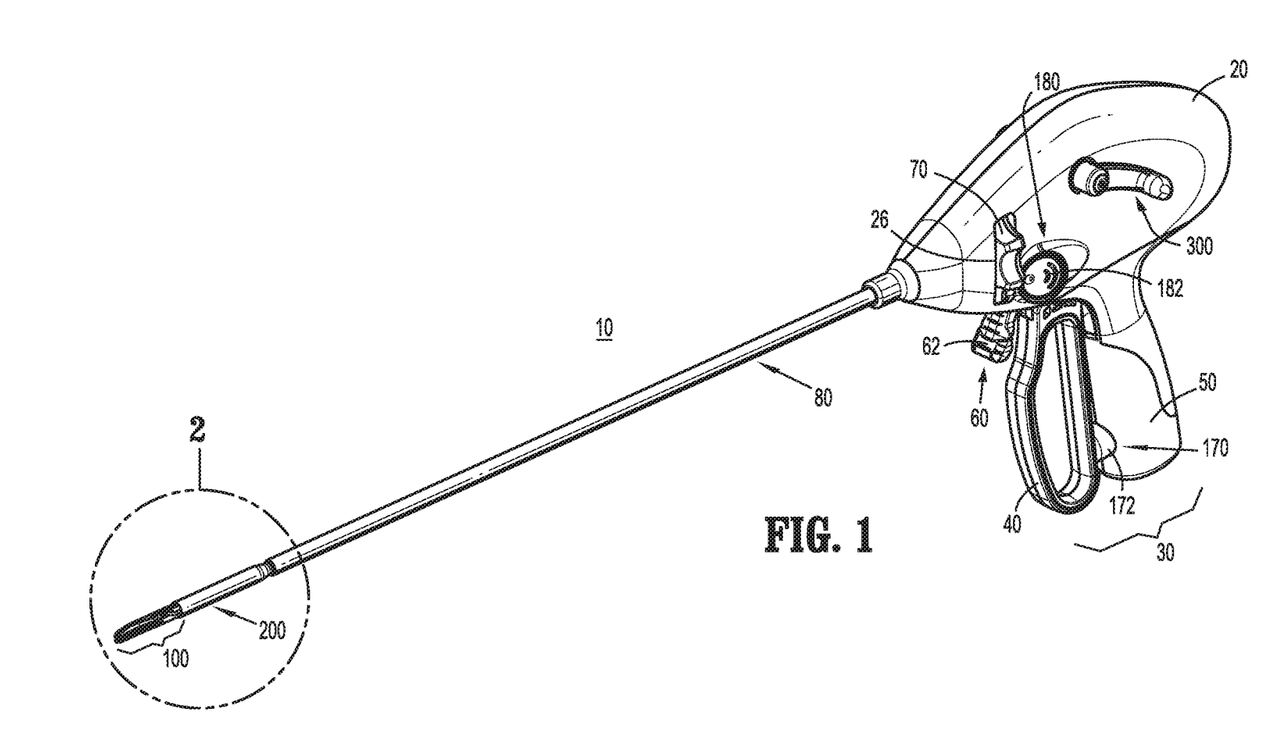
FIG. 1 is a perspective view of an endoscopic surgical instrument provided in accordance with the present disclosure.
Figures 2, 3:
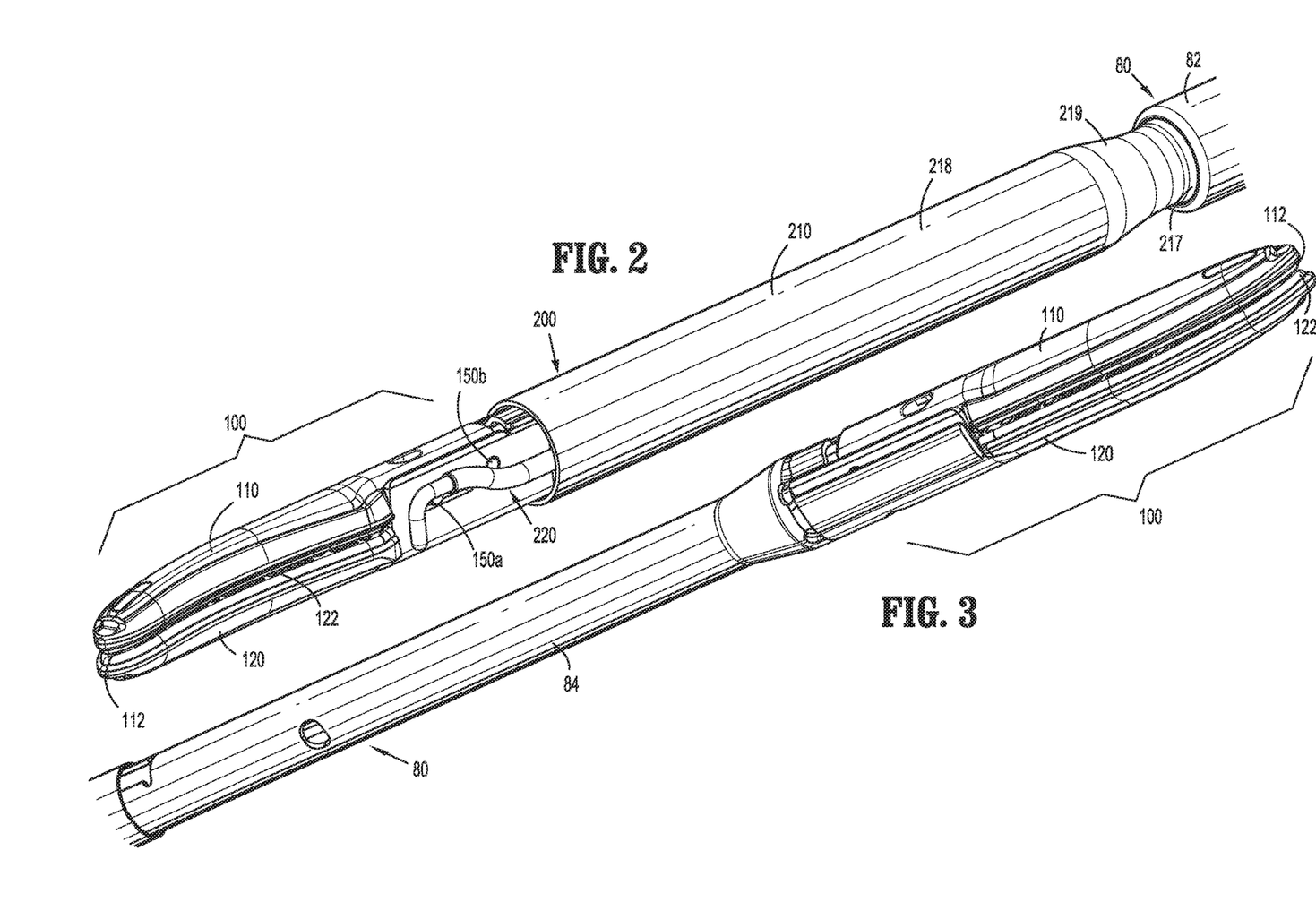
FIG. 2 is an enlarged, perspective view of the area of detail indicated as "2" in FIG. 1.
FIG. 3 is an enlarged, perspective view of the area of detail indicated as "2" in FIG. 1 from the opposite side as illustrated in FIG. 2, with portions removed.
Figure 5:
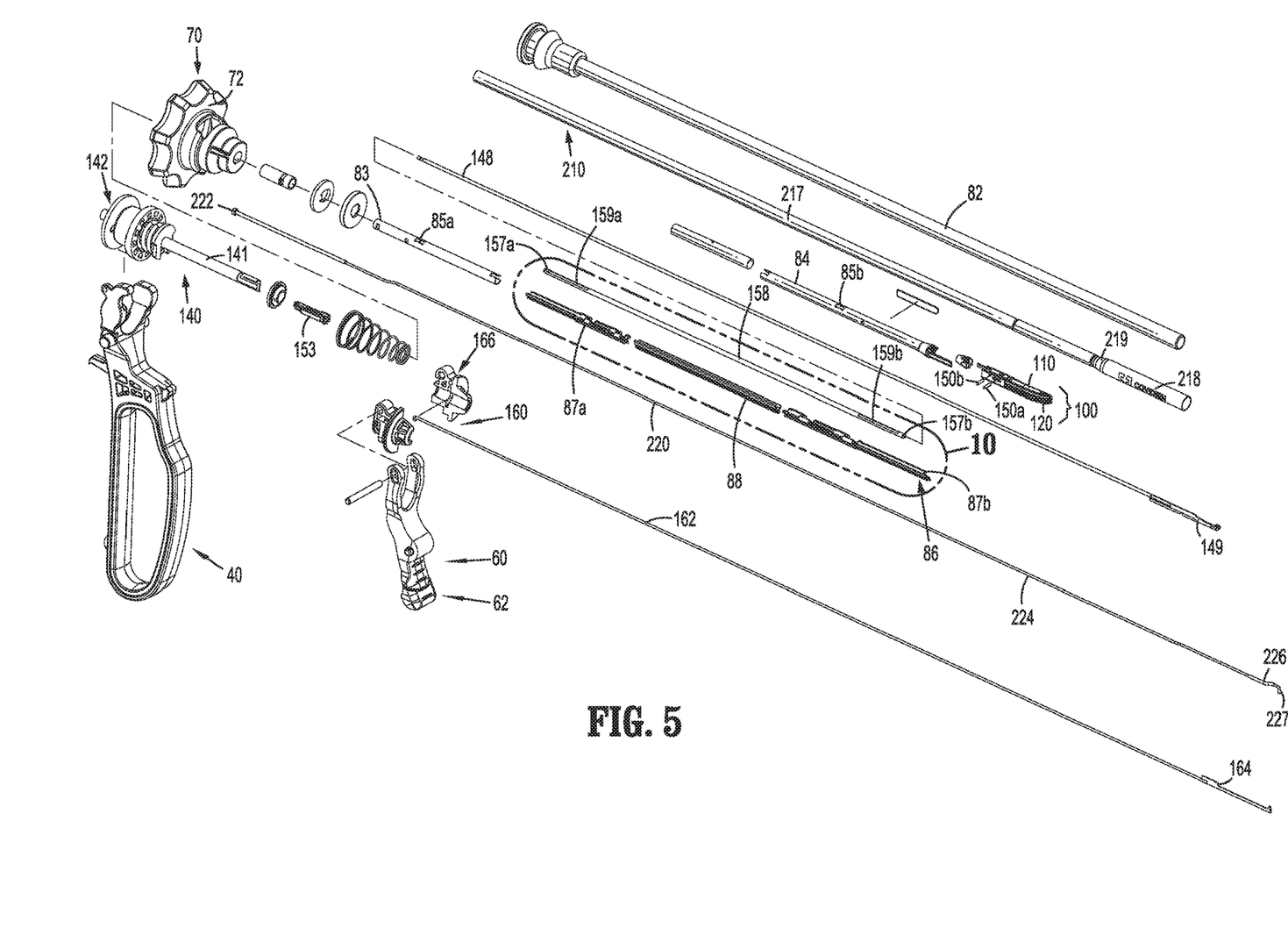
FIG. 5 is an exploded, perspective view of various operable assemblies of the surgical instrument of FIG. 1.
Figure 6:
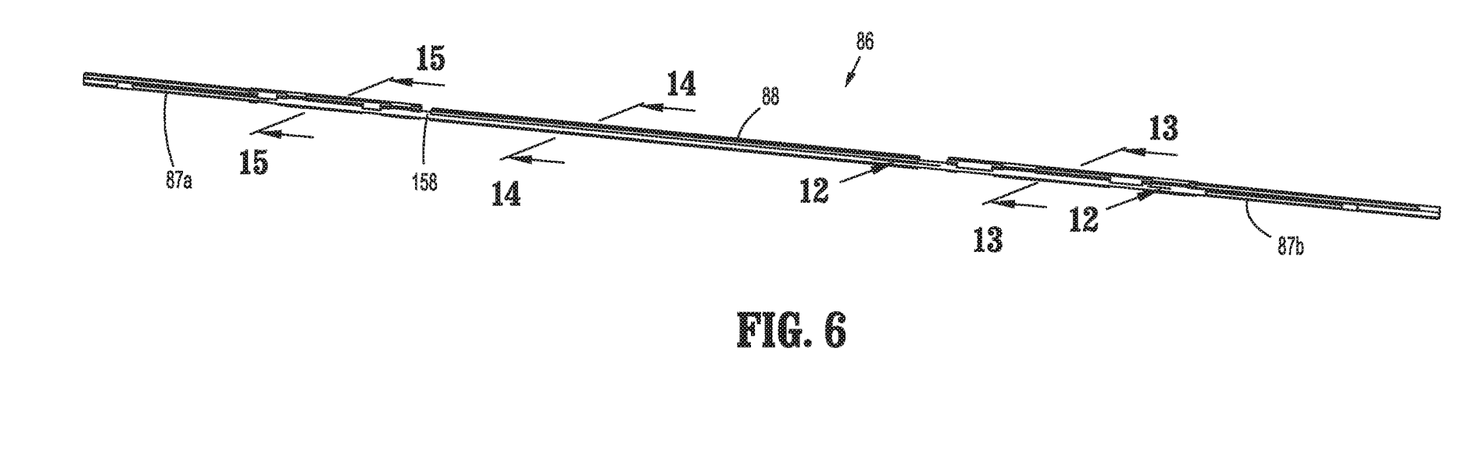
FIG. 6 is a perspective view of a portion of the elongated shaft assembly of the surgical instrument of FIG. 1.
Figure 7:
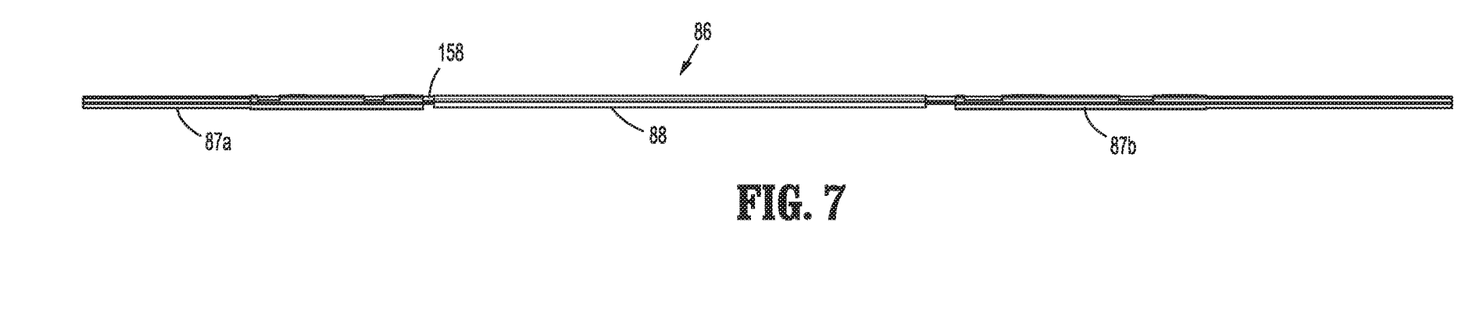
FIG. 7 is a side view of the portion of the elongated shaft assembly illustrated in FIG. 6.
Figure 8:
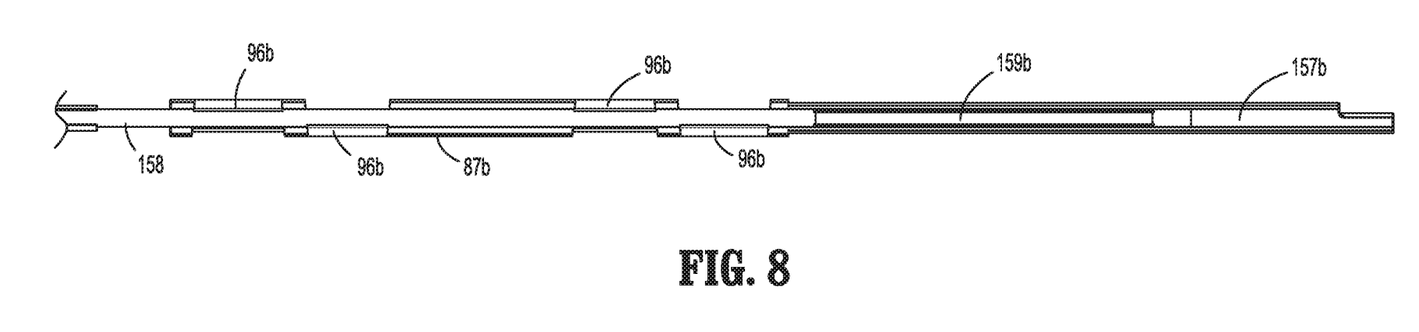
FIG. 8 is an enlarged, top view of a distal portion of the elongated shaft assembly illustrated in FIG. 6.
Figure 9:
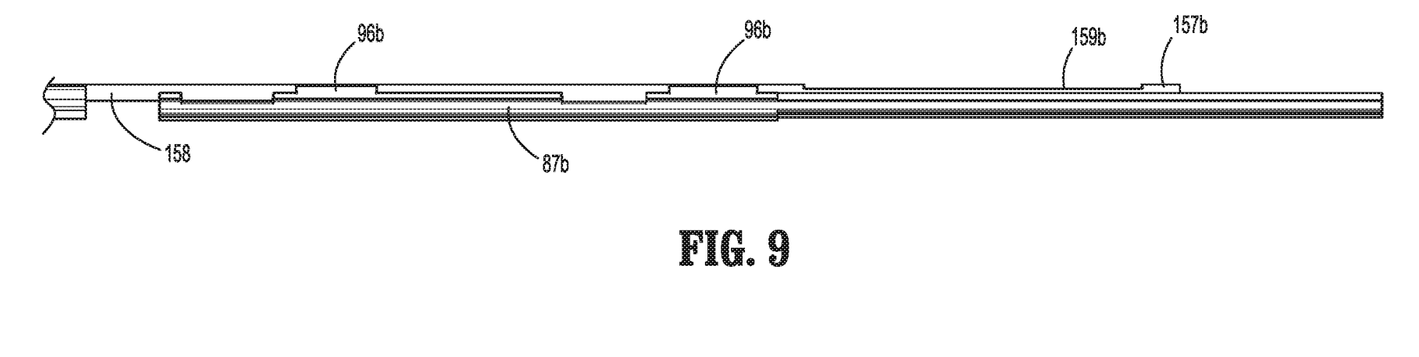
FIG. 9 is an enlarged, side view of the distal portion of the elongated shaft assembly illustrated of FIG. 8.
Figure 10:
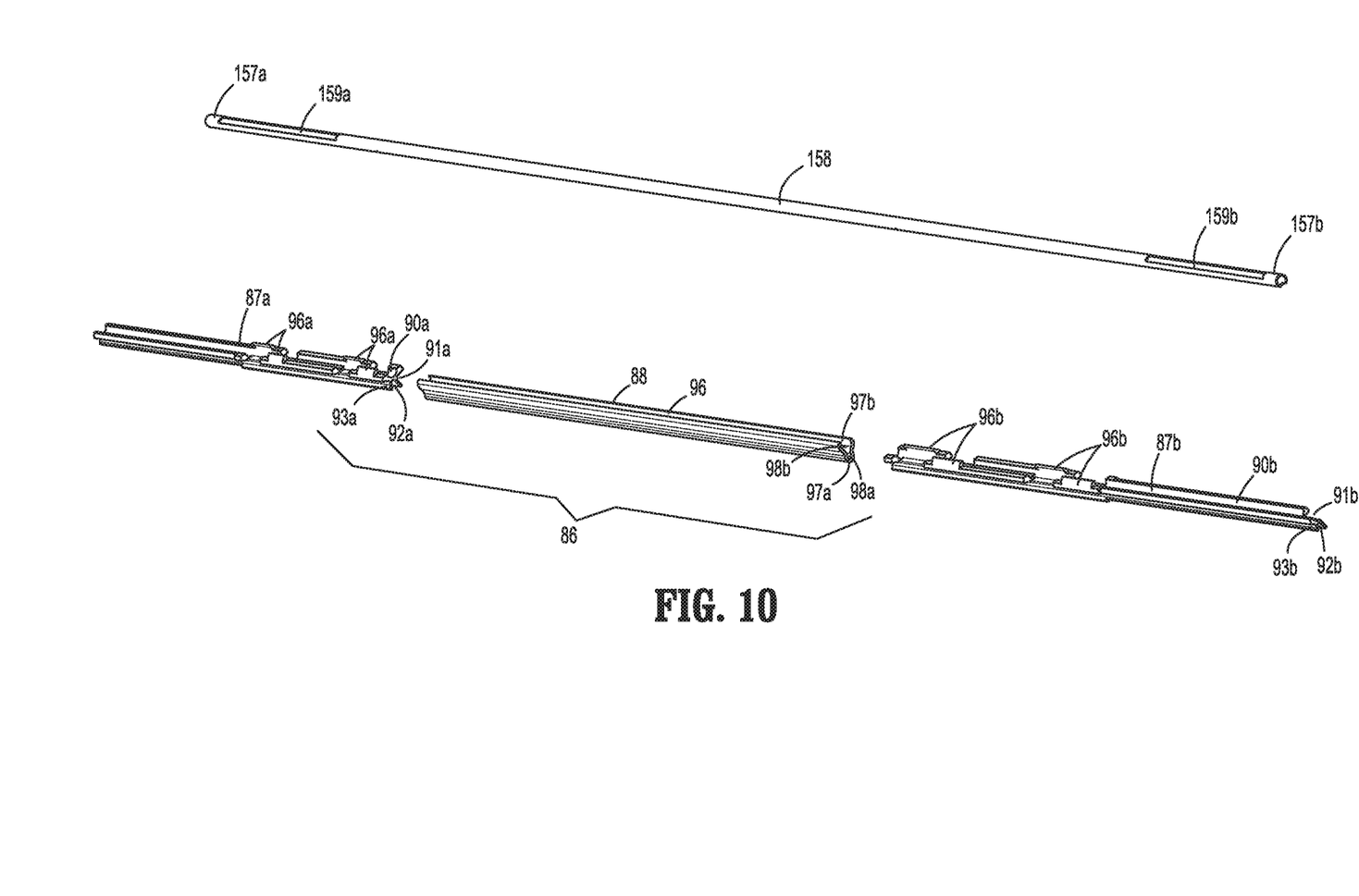
FIG. 10 is an enlarged, exploded, perspective view of the area of detail indicated as "10" in FIG. 5.
Figures 11, 12:
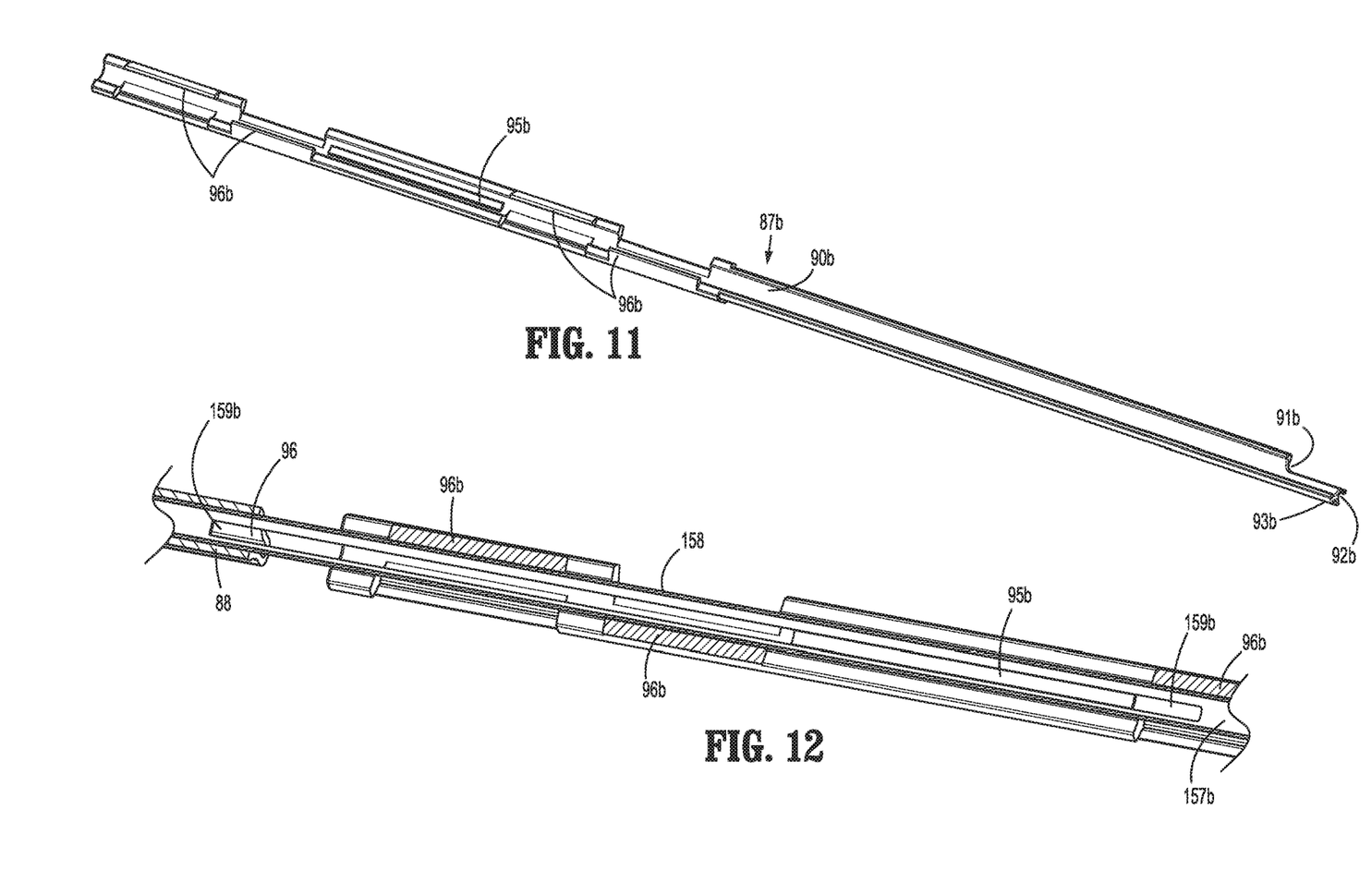
FIG. 11 is an enlarged, perspective view of the distal tube guide of the portion of the elongated shaft assembly illustrated in FIG. 6.
FIG. 12 is an enlarged, longitudinal, cross-sectional view taken along section line "12-12" of FIG. 6.

With reference to FIGS. 2, 3, and 5, end effector assembly 100 is disposed at the distal end of elongated shaft assembly 80 and includes opposing jaw members 110, 120 pivotably coupled to one another. Each of the jaw members 110, 120 includes an electrically-conductive surface 112, 122 adapted to connect to the source of energy (not shown), e.g., via the one or more wires 99 (FIGS. 13-15), and are configured to conduct energy through tissue grasped therebetween. End effector assembly 100 defines a bipolar configuration wherein surface 112 is charged to a first electrical potential and surface 122 is charged to a second, different, electrical potential such that an electrical potential gradient is created for conducting energy between surfaces 112, 122 and through tissue grasped therebetween for treating tissue. Bipolar activation switch 172 of bipolar activation assembly 170 (FIG. 1) is operably coupled between the source of energy (not shown) and surfaces 112, 122 via one or more wires (not shown), thus allowing the selective application of energy to surfaces 112, 122 of jaw members 110, 120, respectively, of end effector assembly 100 during the bipolar mode of operation.

End effector assembly 100 is designed as a unilateral assembly, e.g., where jaw member 120 is fixed relative to elongated shaft assembly 80, e.g., jaw member 120 is engaged with inner distal tube 84 of elongated shaft assembly 80, and jaw member 110 is movable relative to elongated shaft assembly 80 and fixed jaw member 120. However, end effector assembly 100 may alternatively be configured as a bilateral assembly, i.e., where both jaw member 110 and jaw member 120 are movable relative to one another and to elongated shaft assembly 80. Further, in some embodiments, a longitudinally-extending knife channel (not shown) may be defined within one or both of jaw members 110, 120 to permit reciprocation of knife 164 therethrough, e.g., upon actuation of a trigger 62 of trigger assembly 60, to cut tissue grasped between jaw members 110, 120.

Figure 4:
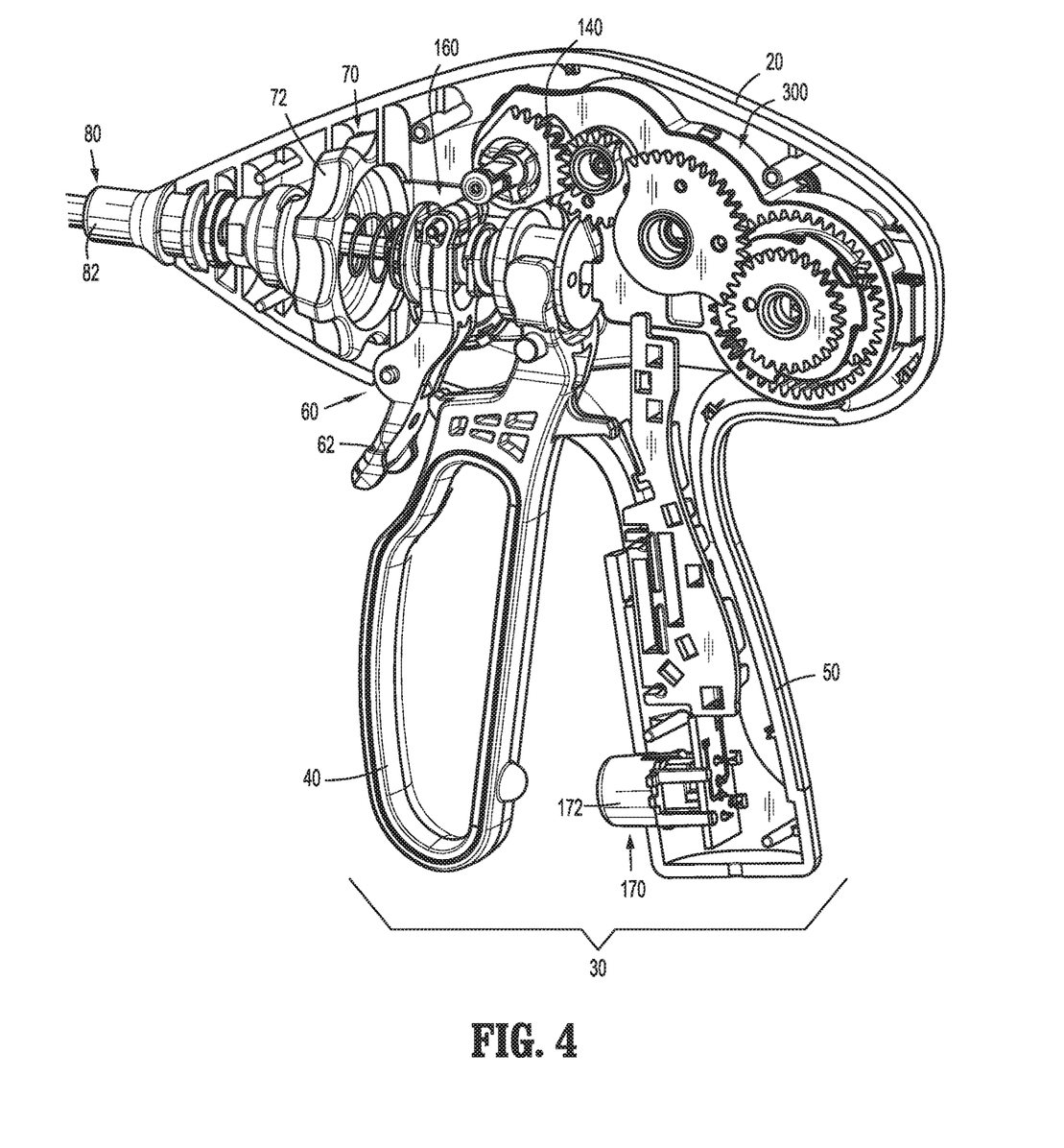
FIG. 4 is a perspective view of the proximal end of the surgical instrument of FIG. 1 with portions removed to illustrate the internal working components thereof.

Referring to FIGS. 1, 4, and 5, handle assembly 30 includes movable handle 40 and a fixed handle 50. Fixed handle 50 is integrally associated with housing 20 and movable handle 40 is movable relative to fixed handle 50 between an initial position, wherein movable handle 40 is spaced-apart from fixed handle 50, and a compressed position, wherein movable handle 40 is compressed towards fixed handle 50.

Referring to FIG. 5, drive assembly 140 includes a proximal sleeve 141 that is slidably disposed within housing 20 (see FIG. 4) and configured to operably couple to movable handle 40. A mandrel assembly 142 of drive assembly 140 operably couples movable handle 40 with proximal sleeve 141 of drive assembly 140. Drive assembly 140 further includes a drive bar 148 operably coupled to end effector assembly 100 at the distal end of drive bar 148 and operably coupled to proximal sleeve 141 at the proximal end of drive bar 148. More specifically, drive bar 148 defines an arm 149 at the distal end thereof that is configured to receive a cam pin 150*a*. Cam pin 150*a*, in turn, is received within corresponding cam slots defined within jaw members 110, 120 such that translation of drive bar 148 relative to end effector assembly 100 translates cam pin 150*a* through the cam slots to thereby pivot jaw member 110 relative to jaw member 120 about pivot pin 150*b*.

Drive bar 148 is operably coupled with proximal sleeve 141 by way of a drive bar support member 153. Drive assembly 140 further includes a support tube 156 disposed about drive bar 148. Support tube 156 defines a proximal end portion 157*a*, a distal end portion 157*b*, a proximal slot 159*a*, and a distal slot 159*b*. Proximal end portion 157*a* of support tube 156 is configured for insertion into inner proximal tube 83 and is secured therein, e.g., via welding through window 85*a* of inner proximal tube 83. Distal end portion 157*b* of support tube 156 is configured for insertion into inner distal tube 84 and is secured therein, e.g., via welding through window 85*b* of inner distal tube 84. Support tube 156, having drive bar 148 extending therethrough, is configured for receipt within first channels 90*a*, 90*b* defined within proximal and distal tube guides 87*a*, 87*b*, respectively, of inner shaft assembly 86 of elongated shaft assembly 80 (see FIGS. 13 and 15), as detailed below.

Referring to FIGS. 1, 4, and 5, trigger 62 of trigger assembly 60 is selectively actuatable relative to housing 20 from an un-actuated position to an actuated position. Knife assembly 160 is operably coupled to trigger 62 such that actuation of trigger 62 from the un-actuated position to the actuated position translates knife 164 of knife assembly 160 from a retracted position, wherein knife 164 is disposed proximally of jaw members 110, 120, to an extended position, wherein knife 164 extends at least partially between jaw members 110, 120 and through the knife channel(s) (not shown) thereof to cut tissue grasped between jaw members 110, 120. Knife assembly 160 includes knife bar 162, knife 164, and a knife collar 166. Knife bar 162 extends proximally from knife 164 and is configured for receipt within fourth channels 93*a*, 93*b* defined within proximal and distal tube guides 87*a*, 87*b* of inner guide assembly 86 of elongated shaft assembly 80 (see FIGS. 13 and 15), as detailed below, such that knife bar 162 extends alongside drive bar 148, spaced-apart therefrom. Knife collar 166 operably couples knife bar 162 with trigger 62 to operably couple trigger assembly 60 and knife assembly 160 with one another such that, upon actuation of trigger 62 from the un-actuated position to the actuated position, knife 164 is translated distally from the retracted position to the extended position to cut tissue grasped between jaw members 110, 120.

Rotation assembly 70 includes rotation wheel 72 that is rotatably disposed but longitudinally constrained within a vertically-oriented slot 26 defined within housing 20 (see FIG. 1). Rotation wheel 72 extends at least partially through slots 26 on either side of housing 20 to enable manipulation of rotation wheel 72 on either exterior side of housing 20 (see FIG. 1). Rotation wheel 72 is engaged about inner proximal tube 83 of elongated shaft assembly 80 such that, as mentioned above, rotation of rotation wheel 72 effects corresponding rotation of inner proximal tube 83, inner distal tube 84, inner guide assembly 86, end effector assembly 100, drive assembly 140, knife assembly 160, and monopolar assembly 200 relative to housing 20 (FIG. 1) and fixed outer tube 82.

With reference to FIGS. 1-5, monopolar assembly 200 includes an insulative sheath 210 and an energizable member 220. Insulative sheath 210 defines a body portion 217, an enlarged-diameter distal portion 218 extending distally from body portion 217, and an annular step 219 disposed therebetween. Insulative sheath 210 is movable relative to end effector assembly 100 between a storage position, wherein insulative sheath 210 is disposed proximally of end effector assembly 100, and a use position, wherein insulative sheath 210 is substantially disposed about end effector assembly 100.

Energizable member 220 of monopolar assembly 200 includes a proximal cap 222, a bar 224, and an energizable element 226 defining a distal tissue-treating portion 227. Energizable element 226 is coupled to the source of energy (not shown) and monopolar activation assembly 180 (FIG. 5) via one or more wires (not shown). Distal tissue-treating portion 227 of energizable element 226 of energizable member 220 functions as the active electrode of monopolar assembly 200. Energizable member 220 slidably extends through second channels 91*a*, 91*b* of proximal and distal tube guides 87*a*, 87*b*, respectively, of inner guide assembly 86 of elongated shaft assembly 80 (see FIGS. 13 and 15), as detailed below.

Energizable member 220 is disposed on the inner-edge side of jaw members 110, 120 of end effector assembly 100 and is movable relative thereto between a storage position, wherein distal tissue-treating portion 227 of energizable member 220 is positioned more-proximally, and a use position, wherein distal tissue-treating portion 227 of energizable member 220 extends distally from end effector assembly 100 to facilitate treating tissue therewith. In the use position, insulative sheath 210 serves to electrically insulate end effector assembly 100 from distal tissue-treating portion 227 of energizable member 220, while distal tissue-treating portion 227 extends distally from end effector assembly 100. Further, in the use position, energy may be supplied to distal tissue-treating portion 227 of energizable member 220, e.g., via activation of either of the activation switches 182 of monopolar activation assembly 180 (FIG. 1), for treating tissue in the monopolar mode of operation.

Referring also to FIGS. 4 and 5, energizable member 220 is engaged with insulative sleeve 210 such that energizable member 220 and insulative sleeve 210 move together between their respective storage and use positions. Further, proximal cap 222 of energizable member 220 is operably coupled to deployment and retraction mechanism 300, thus enabling deployment and retraction mechanism 300 to translate insulative sheath 210 and energizable member 220 between their respective storage positions, collectively the storage condition of monopolar assembly 200, and their respective use conditions, collectively the use condition of monopolar assembly 200.

With reference to FIGS. 6-15, in conjunction with FIG. 5, inner guide assembly 86 of elongated shaft assembly 80 includes proximal and distal tube guides 87*a*, 87*b*, respectively, and tube clip 88. Proximal tube guide 87*a* of inner guide assembly 86 defines first, second, third, and fourth channels 90*a*, 91*a*, 92*a*, 93*a*, respectively, arranged about the outer circumference of proximal tube guide 87*a*. Distal tube guide 87*b* similarly includes first, second, third, and fourth channels 90*b*, 91*b*, 92*b*, 93*b*, respectively, arranged about the outer circumference of distal tube guide 87*b* and aligned with the corresponding channels 90*a*, 91*a*, 92*a*, 93*a* of proximal tube guide 87*a*.

Proximal and distal tube guides 87*a*, 87*b* further include respective ribs 95*a*, 95*b* extending within and along portions of first channels 90a, 90b, respectively, thereof. Ribs 95a, 95b are configured to extend through proximal and distal slots 159a, 159b, respectively, of support tube 156 of drive assembly 140 with support tube 156 extending through first channels 90a, 90b. With ribs 95a, 95b received within proximal and distal slots 159a, 159b, respectively, support tube 156 is longitudinally and rotationally fixed relative to proximal and distal tube guides 87a, 87b and, thus, is maintained in position even if the weld (or other engagement) securing proximal end portion 157a of support tube 156 within inner proximal tube 83 and/or the weld (or other engagement) securing distal end portion 157b of support tube 156 within inner distal tube 84 is faulty. Proximal and distal tube guides 87a, 87b each further include a plurality of retention fingers 96a, 96b alternately disposed therealong. Retention fingers 96a, 96b are configured to enable support tube 156 to snap into engagement within first channels 90a, 90b, although other configurations are also contemplated. As noted above, support tube 156 slidably receives drive bar 148 therethrough and, thus, drive bar 148 is slidably disposed within first channels 90a, 90b of proximal and distal tube guides 87a, 87b, respectively.

As noted above, energizable member 220 slidably extends through second channels 91a, 91b of proximal and distal tube guides 87a, 87b, respectively, and knife bar 162 slidably extends through fourth channels 93a, 93b of proximal and distal tube guides 87a, 87b, respectively. Third channels 92a, 92b of proximal and distal tube guides 87a, 87b, respectively, are configured to receive lead wires 99.

Tube clip 88 of inner guide assembly 86 extends between proximal and distal tube guides 87a, 87b, respectively. Tube clip 88 defines a central channel 96 having a nadir 97a and a mouth 97b opposite nadir 97a. Central channel 96 of tube clip 88 defines a first channel portion 98a and a second channel portion 98b. First channel portion 98a is positioned between nadir 97a and second channel portion 98b, while second channel portion 98b is positioned between first channel portion 98a and mouth 97b. First channel portion 98a defines a reduced width as compared to second channel portion 98b, which expands to a tubular configuration defining a diameter greater than the width of first channel portion 98a. The diameter of second channel portion 98b, more specifically, generally approximates that of support tube 156 of drive assembly 140 to enable complementary engagement of tube clip 88 about a support tube 156 with support tube 156 extending through second channel portion 98b. In some embodiments, tube clip 88 is flexed to accommodate support tube 156 within second channel portion 98b such that tube clip 88 is engaged about support tube 156 under a bias back towards its at-rest position.

Tube clip 88 is positioned relative to proximal and distal tube guides 87a, 87b such that second channel portion 98b is aligned with first channels 90a, 90b of proximal and distal tube guides 87a, 87b, respectively, to enable support tube 156 to extend through first channels 90a, 90b of proximal and distal tube guides 87a, 87b, respectively, and second channel portion 98b of tube clip 88. Tube clip 88 is further positioned relative to proximal and distal tube guides 87a, 87b such that first channel portion 98a is at least partially aligned with third channels 92a, 92b of proximal and distal tube guides 87a, 87b, respectively, to enable third channels 92a, 92b of proximal and distal tube guides 87a, 87b, respectively, and first portion 98a of tube clip 88 to receive and retain lead wires 99 therein. Energizable member 220, on the other hand, slidably extends through second channels 91a, 91b of proximal and distal tube guides 87a, 87b, respectively, along an exterior surface of tube clip 88 on one side thereof, while knife bar 162 slidably extends through fourth channels 93a, 93b of proximal and distal tube guides 87a, 87b, respectively, along an exterior surface of tube clip 88 on a second, opposite side thereof.

The above-detailed configuration of inner guide assembly 86 maintains rotational alignment of the various components extending through elongated shaft assembly 80, inhibits interference between the various components, inhibits twisting of or interference by lead wires 99, and eliminates reliance on welding of components, thus providing an effective and efficient solution for managing the various components extending through elongated shaft assembly 80.

The various embodiments disclosed herein may also be configured to work with robotic surgical systems and what is commonly referred to as "Telesurgery." Such systems employ various robotic elements to assist the surgeon in the operating room and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various drawing figures, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An inner guide assembly for a surgical instrument, comprising:
    a proximal tube guide defining first and second proximal channels extending longitudinally therealong;
    a distal tube guide defining first and second distal channels extending longitudinally therealong, the first and second distal channels disposed in alignment with the first and second proximal channels, respectively; and
    a wire clip disposed between the proximal and distal tube guides, the wire clip defining a central channel having a first portion and a second portion,
    wherein the first proximal channel, the first distal channel, and the first portion of the central channel are configured to cooperate to receive a first elongated component of a surgical instrument longitudinally therethrough, and wherein the second proximal channel, the second distal channel, and the second portion of the central channel are configured to cooperate to receive first and second lead wires of the surgical instrument longitudinally therethrough.

2. The inner guide assembly according to claim 1, wherein at least one of the proximal tube guide or the distal tube guide includes a retention finger configured to retain the first elongated component of the surgical instrument in fixed position relative thereto.

3. The inner guide assembly according to claim 1, wherein at least one of the proximal tube guide or the distal tube guide includes a rib configured to retain the first elongated component of the surgical instrument in fixed position relative thereto.

4. The inner guide assembly according to claim 1, wherein the proximal and distal tube guides further define third proximal and distal channels, respectively, disposed in alignment with one another, the third proximal and distal channels configured to receive a second elongated component of the surgical instrument therethrough externally of the wire clip.

5. The inner guide assembly according to claim 4, wherein the proximal and distal tube guides further define fourth proximal and distal channels, respectively, disposed in alignment with one another, the fourth proximal and distal channels configured to receive a third elongated component of the surgical instrument therethrough externally of the wire clip on an opposite side of the wire clip as the second elongated component.

6. The inner guide assembly according to claim 5, wherein the first, second, third and fourth proximal and distal channels are arranged circumferentially about the proximal and distal tube guides, respectively.

7. The inner guide assembly according to claim 1, wherein the wire clip is oriented such that a mouth of the central channel is oppositely oriented relative to mouths of the second proximal and distal channels and similarly relative to mouths of the first proximal and distal channels.

8. An elongated shaft assembly for a surgical instrument, comprising:
    a proximal tube portion coupled to a manipulation portion of a surgical instrument;
    a distal tube portion coupled to an end effector assembly of the surgical instrument;
    a proximal tube guide at least partially disposed within the proximal tube portion, the proximal tube guide defining first and second proximal channels extending longitudinally therealong;
    a distal tube guide at least partially disposed within the distal tube portion, the distal tube guide defining first and second distal channels extending longitudinally therealong, the first and second distal channels disposed in alignment with the first and second proximal channels, respectively; and
    a wire clip disposed between the proximal and distal tube guides, the wire clip defining a central channel having a first portion and a second portion,
    wherein the first proximal channel, the first distal channel, and the first portion of the central channel are configured to cooperate to receive a first elongated component operably coupled between the manipulation portion and the end effector assembly of the surgical instrument, and wherein the second proximal channel, the second distal channel, and the second portion of the central channel are configured to cooperate to receive first and second lead wires of the surgical instrument longitudinally therethrough to guide the first and second lead wires to the end effector assembly of the surgical instrument.

9. The elongated shaft assembly according to claim 8, further comprising a support tube, wherein the first proximal channel, the first distal channel, and the first portion of the central channel cooperate to receive the support tube therethrough, and wherein the first elongated component of the surgical instrument is slidably disposed within the support tube.

10. The elongated shaft assembly according to claim 9, wherein the first elongated component is disposed in fixed position relative to the proximal tube guide, the distal tube guide, and the wire clip.

11. The elongated shaft assembly according to claim 10, wherein the wire clip is engaged about the first elongated component under a bias.

12. The elongated shaft assembly according to claim 10, wherein at least one of the proximal tube guide or the distal tube guide includes a rib configured to retain the support tube in fixed position relative thereto.

13. The elongated shaft assembly according to claim 8, wherein the proximal and distal tube guides further define third proximal and distal channels, respectively, disposed in alignment with one another, the third proximal and distal channels configured to receive a second elongated component of the surgical instrument therethrough externally of the wire clip, the second elongated component operably coupled to the manipulation portion of the surgical instrument and selectively movable relative to the end effector assembly of the surgical instrument.

14. The elongated shaft assembly according to claim 13, wherein the proximal and distal tube guides further define fourth proximal and distal channels, respectively, disposed in alignment with one another, the fourth proximal and distal channels configured to receive a third elongated component of the surgical instrument therethrough externally of the wire clip on an opposite side of the wire clip as the second elongated component, the third elongated component operably coupled to the manipulation portion of the surgical instrument and selectively movable relative to the end effector assembly of the surgical instrument.

15. A surgical instrument, comprising:
a housing including a first actuator;
an end effector assembly distally-spaced from the housing; and
an elongated shaft assembly extending between and interconnecting the housing and the end effector assembly, the elongated shaft assembly including:
a proximal tube portion coupled to the housing;
a distal tube portion coupled to the end effector assembly;
a proximal tube guide at least partially disposed within the proximal tube portion, the proximal tube guide defining first and second proximal channels extending longitudinally therealong;
a distal tube guide at least partially disposed within the distal tube portion, the distal tube guide defining first and second distal channels extending longitudinally therealong, the first and second distal channels disposed in alignment with the first and second proximal channels, respectively; and
a wire clip disposed between the proximal and distal tube guides, the wire clip defining a central channel having a first portion and a second portion,
wherein the first proximal channel, the first distal channel, and the first portion of the central channel are configured to cooperate to receive a drive shaft operably coupled between the first actuator and the end effector assembly, and wherein the second proximal channel, the second distal channel, and the second portion of the central channel are configured to cooperate to receive first and second lead wires longitudinally therethrough to guide the first and second lead wires to the end effector assembly.

16. The surgical instrument according to claim 15, wherein actuation of the first actuator translates the drive shaft relative to the end effector assembly to manipulate the end effector assembly.

17. The surgical instrument according to claim 15, further comprising a support tube, wherein the first proximal channel, the first distal channel, and the first portion of the central channel cooperate to receive the support tube therethrough, and wherein the drive shaft is slidably disposed within the support tube.

18. The surgical instrument according to claim 15, wherein the proximal and distal tube guides further define third proximal and distal channels, respectively, disposed in alignment with one another, the third proximal and distal channels configured to receive a first deployment shaft therethrough externally of the wire clip, the first deployment shaft operably coupled between a second actuator associated with the housing and a first deployable component selectively deployable relative to the end effector assembly.

19. The surgical instrument according to claim 18, wherein the proximal and distal tube guides further define fourth proximal and distal channels, respectively, disposed in alignment with one another, the fourth proximal and distal channels configured to receive a second deployment shaft therethrough externally of the wire clip on an opposite side of the wire clip as the first deployable component, the second deployment shaft operably coupled between a third actuator associated with the housing and a second deployable component selectively deployable relative to the end effector assembly.

20. The surgical instrument according to claim 15, wherein the elongated shaft assembly further includes a fixed outer tube.

* * * * *